United States Patent [19]
Niwas et al.

[11] Patent Number: 5,189,039
[45] Date of Patent: Feb. 23, 1993

[54] 7-DISUBSTITUTED-METHYL-4-OXO-3H,5H-PYRROLO[3,2D]PYRIMIDINE AND PHARMACEUTICAL USES AND COMPOSITIONS CONTAINING THE SAME

[75] Inventors: Shri Niwas; John A. Secrist, III; John A. Montgomery, all of Birmingham, Ala.; Mark D. Erion, Livingston; Wayne C. Guida, Fanwood, both of N.J.; Steve E. Ealick, Birmingham, Ala.

[73] Assignee: BioCryst, Inc., Birmingham, Ala.

[21] Appl. No.: 701,575

[22] Filed: May 14, 1991

Related U.S. Application Data

[63] Continuation of Ser. No. 42,798, Nov. 29, 1989, abandoned.

[51] Int. Cl.$^5$ .................. A61K 31/503; C07D 471/04
[52] U.S. Cl. ........................... 514/258; 514/234.2; 514/253; 544/117; 544/232; 544/238; 544/244; 544/280; 548/535; 558/404
[58] Field of Search ............... 544/244, 280; 514/258

[56] References Cited

U.S. PATENT DOCUMENTS 4,772,606 9/1988 Sircar et al. ..................... 514/262
4,923,872 5/1990 Kostlan et al. ................... 544/280

Primary Examiner—John M. Ford
Assistant Examiner—Jyothsna Venkat
Attorney, Agent, or Firm—Wegner, Cantor, Mueller & Player

[57] ABSTRACT

Disclosed is a compound of the formula

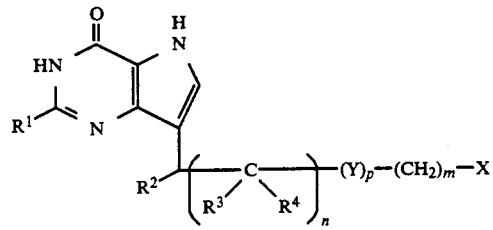

wherein $R^1$ is H, $NH_2$, or $OCH_3$, $R^2$ is an optionally substituted cyclic group optionally containing one or more heteroatoms, $R^3$ and $R^4$ are independently H or $C_{1-4}$ alkyl, m is 0–4, n is 0–6, p is 0.1, X is CN, $CSNH_2$, $PO(OH)_2$, COOH, $SO_2NH_2$, $NH_2$, OH, $CNHNH_2$, tetrazole, triazole, or $COR^5$ where $R^5$ is $C_{1-4}$ alkyl, $CF_3$, $NH_2$, or $OC_{1-4}$ alkyl, and Y is O or NH that is useful as a pharmaceutical.

26 Claims, No Drawings

7-DISUBSTITUTED-METHYL-4-OXO-3H,5H-PYRROLO[3,2D]PYRIMIDINE AND PHARMACEUTICAL USES AND COMPOSITIONS CONTAINING THE SAME

This application is a continuation of U.S. application Ser. No. 07/42,798 filed Nov. 29, 1989, now abandoned.

The present invention relates to derivatives of 4-oxo-3H,5H-pyrrolo[3,2-d]pyrimidine. In particular, it relates to 4-oxo-H,5H-pyrrolo[3,2-d]pyrimidine derivatives substituted at the 7-position.

Purine nucleoside phosphorylase (PNP) catalyzes the phosphorolysis of purine nucleosides in a reversible reaction. Individuals who are deficient in PNP exhibit impaired T-cell development, resulting in lowered cell-mediated immunity, but normal B-cell development, resulting in normal humoral immunity. Accordingly, specific inhibitors of PNP that selectively inhibit T-cell development without damaging humoral immunity could be potentially effective against disorders in which activated T-cells are pathogenic.

Accordingly, the present invention is a compound of the formula

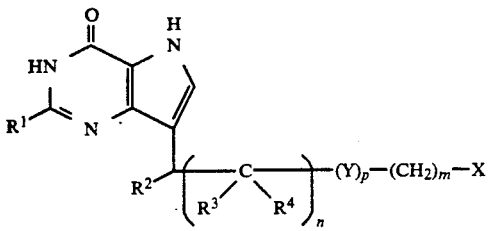

wherein $R^1$ is H, $NH_2$, or $OCH_3$, $R^2$ is an optionally substituted cyclic group optionally containing one or more heteroatoms, $R^3$ and $R^4$ are independently H or $C_{1-4}$ alkyl, m is 0-4, n is 0-6, p is 0-1, X is CN, $CSNH_2$, $PO(OH)_2$, COOH, $SO_2NH_2$, $NH_2$, OH, $CNHNH_2$, tetrazole, triazole or $COR^5$ where $R^5$ is $C_{1-4}$ alkyl, $CF_3$, $NH_2$, or $OC_{1-4}$ alkyl, and Y is O or NH. The compound of the present invention is useful as a PNP inhibitor. Also contemplated according to the present invention are a pharmaceutical composition for the selective suppression of mammalian T-cell immunity comprising a pharmaceutically effective amount of the compound of the present invention and a pharmaceutically acceptable carrier or diluent and a method for the selective suppression of mammalian T-cell immunity without diminished effect on humoral immunity comprising administering to a subject a pharmaceutically effective amount of the compound of the present invention.

The optionally substituted cyclic group (hereinafter referred to as cyclo) recited for the above formula includes aromatic, heteroaromatic, alicyclic, and heteroalicyclic groups preferably containing five to nine atoms. Preferred optional substituents include halogen, hydroxy, alkoxy, alkyl, and trifluoromethyl. Exemplary substituents include chloro, fluoro, methoxy, ethoxy, propoxy, butoxy, methyl, ethyl, propyl, and butyl. Preferred heteroatoms include oxygen, nitrogen, and sulfur, which can be present in combination in the same group. The preferred aromatic and heteroaromatic groups are phenyl, 2- or 3-thienyl, 2- or 3-furanyl, 2-, 3-, or 4-pyridinyl, 2- or 3-pyrrolyl, 2-, 4-, or 5-thiazolyl, 2-pyrazinyl, 3- or 4-pyridazinyl, and 3-, 4-, or 5-pyrazolyl. The preferred alicyclic and heteroalicyclic groups are 1- or 2-adamantyl, cyclohexyl, cycloheptyl, 2- or 3-tetrahydrofuranyl, 2- or 3-tetrahydrothienyl, 2- or 3-tetrahydropyranyl, 2-, 3-, or 4-piperidinyl, 3- or 4-pyrazolidinyl, 2-, 4-, or 5-thiazolidinyl, 2- or 3-piperazinyl, 2- or 3-morpholinyl, or 3- or 4-hexahydropyridazinyl.

The present invention contemplates pharmaceutical compositions suitable for enteral, such as oral or rectal, transdermal and parenteral administration to mammals including man, which are useful to inhibit purine nucleoside phosphorylase activity and for the treatment of disorders responsive thereto, comprising an effective amount of a pharmacologically active compound of the invention, alone or in combination, with one or more pharmaceutically acceptable carriers.

Preferred pharmaceutical compositions are tablets and gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with a carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Another aspect of the present invention provides a method of making a 2-amino compound ($R^1=NH_2$) of the present invention and intermediates thereof. The first step of the method involves reacting an optionally substituted cyclic aldehyde with cyanoacetic acid at a molar ratio of about 1/1 to 1/5 in the presence of ammonium acetate at about reflux temperature for about 10 hours to 8 days to make a 3-cyclo-substituted pentanedinitrile as an intermediate. In the second step, the 3-cyclo-pentanedinitrile is reacted with an alkyl formate such as ethyl formate and a strong base such as the metal-containing bases sodium hydride or sodium alkoxide, e.g., sodium methoxide, at a molar ratio of about 1-2/3-6/1-3 and at a temperature of about 20°-65° C. for about 10 hours to 8 days to make a 3-cyclo-2-formylpentanedinitrile as a further intermediate. The next step involves reacting the 3-cyclo-2-formylpentanedinitrile with a glycine alkyl ester hydrochloride and sodium or ammonium acetate at a molar ratio of about 1-2/1.5-4/1.5-4 and at a temperature of about 20°-60° C. for about 10-48 hours to make methyl N-[(3-cyclo-2,4-dicyano)-2-butenyl]glycine as an intermediate. In the subsequent step, the methyl N-[(3-cyclo-2,4-dicyano)-2-butenyl]glycine is reacted with an alkyl chloroformate such as ethyl chloroformate and 1,5-diazabicyclo[4.3.0]non-5-ene (DBN) or 1,8-diazabicyclo[5.4.0]undec-7-ene (DBU) at a molar ratio of about 1-2/1.5-5/1.5-4 and at a temperature of about 0°-50° C. for about 10 hours to 10 days to make methyl 3-amino-4-(2-cyano-1-cyclo-ethyl)-1-ethyl-1H-pyrrole-1,2-dicarboxylate as an intermediate. The next step involves reacting the methyl 3-amino-4-(2-cyano-1-cyclo-ethyl)-1-ethyl-1H-pyrrole-1,2-dicarboxylate with a base such as sodium carbonate at a molar ratio of about 2/1 to 1/5 and at about room temperature for about 10-48 hours to make methyl 3-amino-4-(2-cyano-1-cyclo-ethyl)-1H-pyrrole-2-carboxylate as an intermediate. In the next step, the methyl 3-amino-4-(2-cyano-1-cyclo-ethyl)-1H-pyrrole-2-carboxylate is reacted with benzoylisothiocyanate at a molar ratio of about 2/1 to ½ and at about room temperature for about 30 minutes to 3 hours to make N-benzoyl-N'-[4-(2-cyano-1-cyclo-ethyl)-2-methoxycarbonyl-1H-pyrrol- 3-yl]thiourea as an intermediate. The next step reacts the N-benzoyl-N'-[4-(2-cyano-1-cyclo-ethyl)-2-methoxycarbonyl-1H-pyrrol-4-3-yl]thiourea with an alkyl halide such as methyl iodide at a molar ratio of about 1/1 to 1/6 and at a temperature of about 0°-30° C. for about 10 minutes to 10 hours to make N-benzoyl-N'-[4-(2-cyano-1-cyclo-ethyl)-2-methoxycarbonyl-1H-pyrrol-3-yl]S-methylthiourea as an intermediate. In the following step, the N-benzoyl-N'-[4-(2-cyano-1-cyclo-ethyl)-2-methoxycarbonyl-1H-pyrrol-3-yl]-S-methylthiourea (about 1-2 mol) is reacted with methanolic or ethanolic ammonia at a ratio of about 1/1 to 1/20 and at a temperature of about 20°-130° C. for about 16-60 hours to make a mixture of a 2-amino compound of the present invention 3-cyclo-3-[2-amino-4-oxo-3H-5H-pyrrolo[3,2-d]pyrimidin-7-yl]propanenitrile and a 3-cyclo-3-[2-methylmercapto-4-oxo-3H,5H-pyrrolo[3,2-d]pyrimidin-7-yl]propanenitrile as an intermediate in making another compound of the present invention.

In a further aspect of the present invention there is provided a method of making a 2-methoxy compound ($R^1=OCH_3$) and intermediates thereof. The intermediate 3-cyclo-3-[2-methylmercapto-4-oxo-3H,5H-pyrrolo[3,2-d]pyrimidin-7yl]propanenitrile is reacted with an oxidizing agent such as permanganate or hydrogen peroxide at a molar ratio of about 1/1 to 1/10 and at a temperature of about 25°-120° C. for about 3-48 hours to make 3-cyclo-3-[2-methylsulfonyl-4-oxo-3H,5H-pyrrolo[3,2-d]pyrimidin-7-yl]propanenitrile as an intermediate. In the next step, the 3-cyclo-3-[2-methylsulfonyl-4-oxo-3H,5H-pyrrolo[3,2-d] pyrimidin-7-yl]propanenitrile is reacted with a sodium alkoxide such as sodium methoxide at a molar ratio of about 1/1 to 1/10 and at a temperature of about 25°-100° C. for about 1-48 hours to make a 2-methoxy compound of the present invention 3-cyclo-3-[2-methoxy-4-oxo-3H,5H-pyrrolo[3,2-d]pyrimidin-7-yl]propanenitrile.

In a further aspect of the present invention there is provided a method of making a compound of the present invention wherein $R^1$ is hydrogen. The methyl 3-amino-4-(2-cyano-1-cyclo-ethyl)-1H- pyrrole-2-carboxylate intermediate described supra is reacted with dimethylformamide dimethyl acetal at a molar ratio of about 1/1 to ¼ and at a temperature of about 25°-100° C. for about 1-10 days to make methyl 4-(2-cyano-1-cyclo-ethyl)-3-[N(dimethylaminomethylene)amino]-1H-pyrrole-2-carboxylate as an intermediate. The next step involves reacting the methyl 4-(2-cyano-1-cyclo-ethyl)-3-[N-(dimethylaminomethylene)amino]-1H-pyrrole-2-carboxylate with methanolic or ethanolic ammonia at a molar ratio of about 1/1 to 1/20 and at a temperature of about 20°-130° C. for about 10-68 hours to make the compound of the present invention 3-cyclo-3-[4-oxo-3H,5H-pyrrolo[3,2-d[pyrimidin-7-yl]propanenitrile.

As will be apparent to the skilled artisan, variations of the aforesaid procedures are useful in making the variety of compounds of the present invention without departing from the spirit thereof. For example, compounds having different values for "n" and "m" in accordance with the present invention are obtained by either stepping up or stepping down the series by the necessary number of carbon atoms in accordance with known procedures. Also, reactions involving some intermediates require protection of nitrogen or oxygen atoms on the intermediates using known procedures.

The present invention provides a method of inhibiting purine nucleoside phosphorylase activity in mammals which comprises administering to a mammal in need thereof an effective amount of a compound of the invention or of a pharmaceutical composition comprising a said compound in combination with one or more pharmaceutically acceptable carriers. Diseases and conditions responsive to purine nucleoside phosphorylase activity include, e.g., autoimmune disorders, rejection of transplantation and psoriasis.

A further aspect of the invention relates to a method of inhibiting the phosphorolysis and metabolic breakdown of antiviral or antitumor purine nucleosides in mammals which comprises administering in conjunction therewith to a mammal in need thereof, either separately or in combination therewith, an effective purine nucleoside phosphorylase inhibiting amount of a compound of the invention or of a said compound in combination with one or more pharmaceutically acceptable carriers. More particularly, such relates to a method of inhibiting the phosphorolysis and metabolic breakdown of purine nucleosides known in the art, e.g., of 2'-deoxyguanosine, 2',3'-dideoxyinosine, 2',3'-dideoxyguanosine or 2',3'-dideoxyadenosine.

Furthermore, the invention thus relates to a method of potentiating the antiviral or antitumor effect of 2' or 3'-monodeoxypurine nucleosides or of 2',3'-dideoxypurine nucleosides in mammals which comprises administering in conjunction therewith to a mammal in need thereof, either separately or in combination with a said nucleoside, an effective purine nucleoside phosphorylase inhibiting amount of a compound of the invention preferably in combination with one or more pharmaceutically acceptable carriers. More particularly, such relates to a method of enhancing or potentiating the effect of 2',3'-dideoxypurine nucleosides known in the art, e.g., of 2',3'-dideoxyinosine, 2',3'-dideoxyguanosine or 2'-3'-dideoxyadenosine which are used for the treatment of retrovirus infections, e.g., HIV-retrovirus infections (acquired immunodeficiency syndrome, AIDS). 2',3'-Dideoxypurine nucleosides are known in the art as inhibitors of HIV retrovirus infectivity and to be metabolically degraded by PNP, e.g., as described in *Biochemical Pharmacology* Vol. 36, No. 22, 3797 (1987).

Such are administered at a pharmaceutically acceptable dose which is effective in inhibiting HIV-retrovirus infections. Preferably the lowest possible effective dose is used.

The pharmaceutically acceptable effective dosage of active compound of the invention to be administered is dependent on the species of warm-blooded animal (mammal), the body weight, age and individual condition, and on the form of administration.

The pharmaceutical composition may be oral, parenteral, suppository or other form which delivers the compound of the present invention into the bloodstream of a mammal to be treated. An oral form has from about 1 to about 150 mg of the compound of the present invention for an adult (50 to 70 kg) which is mixed together with pharmaceutically acceptable diluents such as lactose. In a typical capsule, 25 mg of the compound of the present invention is mixed together with 192 mg lactose, 80 mg modified starch and 3 mg magnesium stearate. Injectable forms of the compound are also contemplated for administration.

The present invention is also useful with other therapeutic agents. A daily dosage of the compound of the present invention for a human weighing 50 to 70 kg of 1–50 mg/kg inhibits metabolic destruction of certain anticancer agents such as $\beta$-2'-deoxy-6-thioguanosine and antiviral agents such as 2',3'-dideoxyinosine, an anti-AIDS drug. These types of agents are known to be susceptible to cleavage. Upon cleavage, the agents lose effectiveness. The compounds of the present invention are capable of reducing such cleavage. This protection, therefore, enhances the efficacy of other chemotherapeutic agents.

In order to more fully describe the present invention the following non-limiting examples are provided. In the examples all parts and percentages are by weight unless indicated otherwise. Proportions of solvent mixtures used as chromatographic eluents are by volume.

EXAMPLE 1

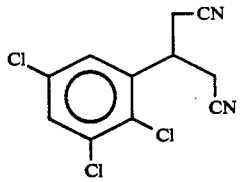

The above intermediate compound is prepared in this Example by the modification of the procedure of Schiemenz, G. P.; Engelhard, H. (*Chem. Ber.*, 1962, 95, 195).

A mixture of cyanoacetic acid (25.38 g, 298.38 mmol), 2,3,5-trichlorobenzaldehyde (25.0 g, 119.35 mmol), ammonium acetate (500 mg), toluene (120 ml), and pyridine (65 ml) is heated at reflux for 16 h in a flask fitted with Dean-Stark trap and condenser. The solvents are evaporated in vacuo, residue is extracted with CHCl$_3$, which is washed with H$_2$O, dried (Na$_2$SO$_4$) and evaporated to give the crude product, which is purified by silica gel column chromatography using hexane-EtOAc mixture as the eluent. Yield 23.69 g (73%); mp 90°–91° C.

EXAMPLE 2

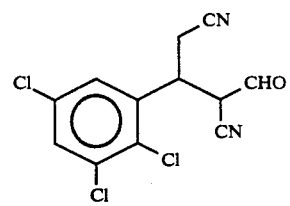

The above intermediate compound is prepared in this Example. To a stirred mixture of NaH (1.56 g, 65.05 mmol) and ethyl formate (14.78 199.51 mmol) in THF (100 ml) is added substituted pentanedinitrile of Example 1 (10.17 37.17 mmol) at room temperature under a nitrogen atmosphere, and the resulting reaction mixture is stirred for 24 h. Volatile matter is evaporated in vacuo at room temperature. Water (50 ml) is added to the residue at 0°–5° C., and the solution is adjusted to pH 5–6 by 20% conc. HCl (v/v). The heavy oil is extracted into ethyl acetate, washed with H$_2$O (1×100 ml) and dried (MgSO$_4$). The ethyl acetate layer is evaporated to give a red-brown oil (11.0 g) that is used in the next step without further purification.

EXAMPLE 3

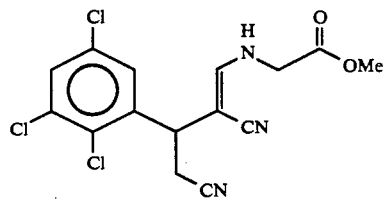

The above intermediate compound is prepared in this Example. Glycine methyl ester hydrochloride (8.17 g, 65.06 mmol) and sodium acetate (5.33 g, 65.06 mmol) are added to a solution of the crude formyl compound of Example 2 (11.0 g) in a mixture of MeOH (80 ml) and H$_2$O (20 ml), and the resulting solution is stirred at room temperature for 22 h. After evaporation of solvent at room temperature, the residue is extracted with ethyl acetate. The washed (H$_2$O) and dried (MgSO$_4$) organic layer is evaporated to give an oil. Flash column chromatography (silica gel) using CHCl$_3$ as eluent gave the pure desired enamine as a mixture of cis-trans isomers which is recrystallized from MeOH, yield 10.41 g (75%), mp 142°–143° C.

EXAMPLE 4

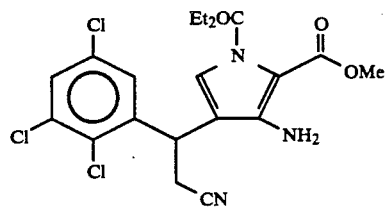

The above intermediate compound is prepared in this Example. A solution of enamine of Example 3 (10.0 g, 26.84 mmol) in dry CH$_2$Cl$_2$ (100 ml) is cooled to 0° C. and treated with 1,5-diazabicyclo[4.3.0]non-5-ene (10.53 g, 84.79 mmol) under a nitrogen atmosphere followed by ethyl chloroformate (6.90 g, 63.57 mmol). The solution is stirred at 0° C. for 1 h and then at room temperature for 48 h. Volatiles are evaporated in vacuo to give a viscous dark gum which is purified by flash column chromatography over silica gel using CHCl$_3$ as the eluent. All the fractions containing the desired N-protected pyrrole are pooled and evaporated to give a foamy light pale yellow material which is stirred in MeOH (100 ml) to give the crystalline material which is recrystallized from CHCl$_3$—MeOH, yield 8.92 (74.7%), mp 160°–161° C.

EXAMPLE 5

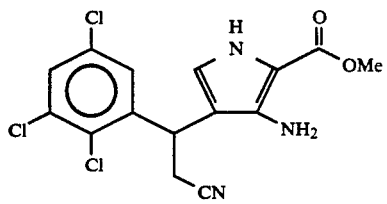

The above intermediate compound is prepared in this Example. A suspension of N-protected pyrrole of Example 4 (8.6 g, 19.34 mmol) in MeOH (300 ml) is treated with Na$_2$CO$_3$ (5.12 g, 48.34 mmol) and the reaction mixture is stirred at room temperature for 17 h with separation of the deblocked pyrrole during the first hour. Solid sodium carbonate is removed by filtration and washed well with MeOH. The filtrate is reduced to a volume of ~25 ml and kept in a refrigerator for 1 h to give 5.23 g of crystalline product. Further concentration of the mother liquor gave an additional 0.14 g of pure product; total yield 6.45 g (89.5 %), mp 178°–181 C.

EXAMPLE 6

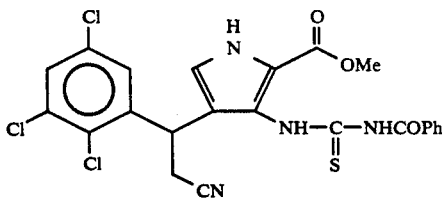

The above intermediate compound is prepared in this Example. To a suspension of pyrrole of Example 5 (5.83 g, 15.64 mmol) in dichloromethane (100 ml) is added benzoylisothiocyanate (2.88 g, 17.64 mmol) at room temperature under nitrogen. The reaction mixture is stirred for 30 min with the separation of the desired thioureido compound. Additional benzoyl isothiocyanate (0.5 ml) is added to it and again stirred for 30 min. The solvent is evaporated to dryness, and the light yellow residue is triturated with methanol. The white crystalline material is isolated by filtration and recrystallized from a chloroform-ether mixture to give the required thioureido compound as an analytically pure sample, yield 7.71 g (92%), mp 210°–211° C.

EXAMPLE 7

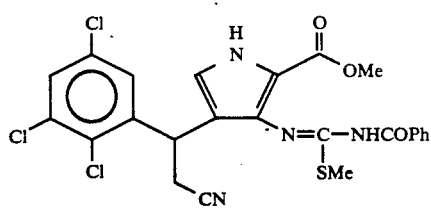

The above intermediate compound is prepared in this Example. A solution of thioureido compound of Example 6 (6.75 g, 12.6 mmol) and 1,5-diazabicyclo[4.3.0]-non-5-ene (1.76 g, 14.20 mmol) in dry CH$_2$Cl$_2$ (200 ml) is cooled to 0° C. and treated with methyl iodide (5.20 g, 36.65 mmol). The reaction mixture is stirred at 0° C. for 10 min and then for 1 h at room temperature. The solvent is evaporated at room temperature, and the residue is extracted with CHCl$_3$, washed with H$_2$O (2×50 ml), dried (Na$_2$SO$_4$) and evaporated to give a glassy foam (6.95 g) which is used in the next step without purification.

EXAMPLE 8

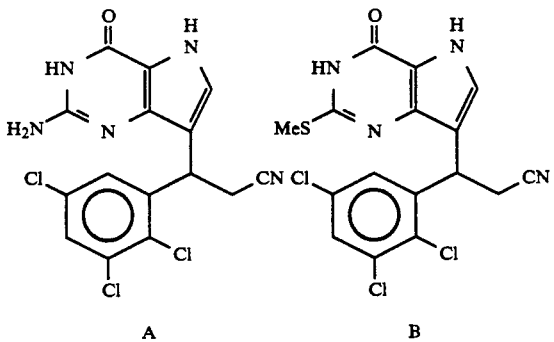

The above compounds A and B are prepared in this Example. The compound A is a compound of the present invention and the compound B is an intermediate. A solution of the methylthio intermediate of Example 7 (6.90 g, 12.54 mmol) in MeOH (200 ml) is saturated at 0° C. with ammonia and heated at 100° C. for 20 h in a glass-lined stainless steel bomb. The reaction mixture is brought to room temperature and the solvent is evaporated at room temperature. Purification of the crude mixture by flash column chromatography over silica gel using CHCl$_3$ as eluent gave 8B (1.1 g, 21%), mp 290°–291° C. then CHCl$_3$—MeOH (95:5) gave pure 8A (2.76 g, 57.5%), mp 284°–285° C.

EXAMPLE 9

The compound of the present invention of Example 8 is tested for enzyme inhibition activity. A purine nucleoside phosphorylase (PNP) enzyme assay is performed in which the PNP activity (IC$_{50}$) for the compound (8A) is found, which is determined radiochemically by measuring the formation of [$^{14}$C]-hypoxanthine from [$^{14}$C]-inosine (see *Biomedicine*, 1980, 33, 39) using calf spleen as the enzyme source. At 1 mM phosphate the IC$_{50}$ is 0.64 μM and at 50 mM phosphate the IC$_{50}$ is 10 μM.

EXAMPLE 10

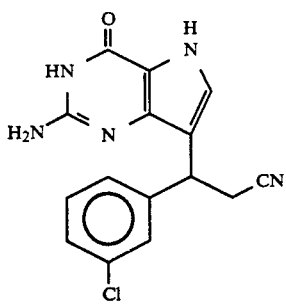

Following the procedure set forth in Examples 1–8, 3-(3-chlorophenyl)-3-(2-amino-4-oxo-3H,5H-pyrrolo[3,2-d]pyrimidin-7-yl)propanenitrile (IC) is prepared using 3-(3-chlorophenyl)pentanedinitrile as the starting material, yield 54.5%, mp 157°–158° C.

EXAMPLE 11

Following the procedure set forth in Examples 1–8, the following compounds are also prepared (1–9).

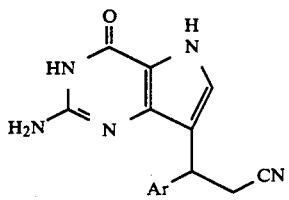

Where Ar is each of the following: (1) phenyl, 2,3-dichlorophenyl, 3-methylphenyl, and 3-methoxyphenyl, (2) thienyl (2- and 3-), (3) furanyl (2- and 3-), (4) pyridinyl (2-, 3-, and 4-), (5) pyrrolyl (2- and 3-), (6) thiazolyl (2-, 4-, and 5-), (7) 2-pyrazinyl, (8) pyridazinyl (3- and 4-), and (9) pyrazolyl.

EXAMPLE 12

Following the procedure set forth in Examples 1–8, the following compounds 10–14 and 21 are prepared starting from the appropriately substituted pentanedinitrile. Compounds 15–20, and 22 are prepared from the corresponding unsaturated Ar analogues in Example 11. In this procedure, the nitrile group of the unsaturated analogue is first converted to an amide group by acid- or base-catalyzed hydrolysis, then the unsaturated Ar group is converted to the saturated $R^2$ group by known catalytic hydrogenation, followed by reconverting the amide back to the nitrile by known dehydration procedures.

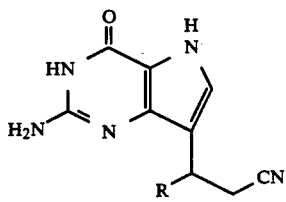

3-(Substituted)-3-(2-amino-4-oxo-3H, 5H-pyrrolo[3, 2-d]-pyrimidin-7-yl)propanenitrile Where $R^2$ is each of: 10) 1-adamantyl, 11) 2-adamantyl, 12) cyclohexyl, 13) cycloheptyl, 14) cyclopentyl, 15) tetrahydrofuranyl, 16) tetrahydrothienyl, 17) tetrahydropyranyl, 18) pyrazolidinyl, 19) thiazolidinyl, 20) piperazinyl, 21) morpholinyl, and 22) hexahydropyridazinyl.

EXAMPLE 13

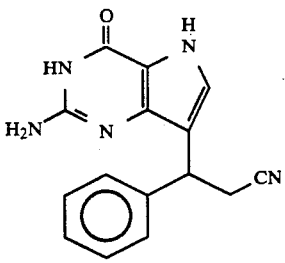

The above compound, 3-(2-amino-4-oxo-3H,5H-pyrrolo[3,2-d]pyrimidin-7-yl)-3-phenylpropanenitrile, is prepared in this Example. A solution of the compound A obtained in Example 8 (2.0 g, 5.22 mmol) in warm ethanol (250 ml) and dimethylformamide (DMF) (150 ml) is hydrogenated over 30% Pd/C catalyst (1.0 g) in the presence of triethylamine (2.64 g, 5.0 equivalent) at atmospheric pressure. After 5 h, the reaction is complete, and the catalyst is filtered off under $N_2$ pressure. The solid obtained by evaporation of the filtrate is triturated and sonicated with $H_2O$ and dried, yield 1.28 g (88%), mp 168°–170 ° C.

EXAMPLE 14

The compound prepared in Example 13 is tested for enzyme inhibition activity as in Example 9. At 1 mM phosphate the $IC_{50}$ is 0.023 $\mu$M and at 50 mM phosphate the $IC_{50}$ is 4.7 $\mu$M.

EXAMPLE 15

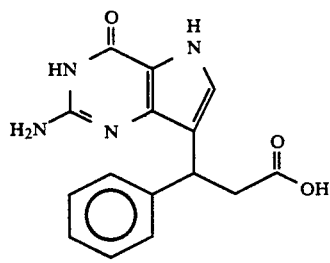

The above compound, 3-(2-amino-4-oxo-3H,5H-pyrrolo[3,2-d]pyrimidin-7-yl)-3-phenylpropanoic acid, is prepared in this example. A solution of the compound obtained in Example 13 (0.200 g, 0.72 mmol) in 6N HCl (3.0 ml) is heated at reflux for 18 h. The solvent is evaporated in vacuo and the residue is triturated with $H_2O$ (6 ml), adjusted to pH ≈10 by conc. ammonium hydroxide. Insoluble material is collected by filtration and the filtrate is readjusted to pH ~6.8. White material which is precipitated out is collected, washed with water and dried, yield 0.19 g (89%), mp 290° C. dec.

EXAMPLE 16

The compound prepared in Example 15 is tested for enzyme inhibition activity as in Example 9. At 1 mM phosphate the $IC_{50}$ is 0.012 $\mu$M and at 50 mM phosphate the $IC_{50}$ is 0.19 $\mu$M.

EXAMPLE 17

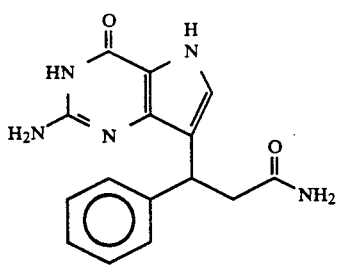

The above compound, 3-(2-amino-4-oxo-3H,5H-pyrrolo[3,2-d]pyrimidin-7-yl)-3-phenylpropanamide, is prepared in this example. A solution of the compound obtained in Example 13 (0.200 g, 0.72 mmol) in conc. $H_2SO_4$ (0.5 ml) is stirred at room temperature for 20 h and then poured onto crushed ice (5.0 g) and adjusted to pH ~6.8 by conc. $NH_4OH$. The precipitated solid is collected, washed with $H_2O$ and dried, yield 0.180 g, mp 199°-201 ° C. dec.

EXAMPLE 18

The compound prepared in Example 17 is tested for enzyme inhibition activity as in Example 9. At 1 mM phosphate the $IC_{50}$ is 0.20 μM and at 50 mM phosphate the $IC_{50}$ is 6.6 μM.

EXAMPLE 19

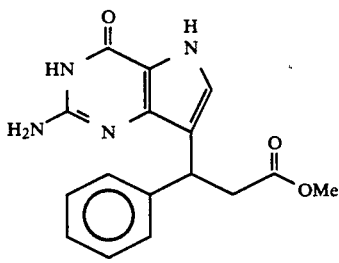

The above compound, 3(2-amino-4-oxo-3H,5H-pyrrolo[3,2-d]pyrimidin-7-yl)-3-phenylpropanoic acid, methyl ester, is prepared in this example. Thionyl chloride (0.2 g, 0.17 mmol) is added to stirred methanol (4.0 ml) at 0° C. The compound obtained in Example 15 (0.2 g, 0.67 mmol) is added and the mixture is stirred at room temperature for 18 h. The solvent is removed on a water aspirator (30° C.) and vacuum pump (lyophilize) to give a semisolid mass which is purified on a silica gel column using $CHCl_3$—MeOH as the eluent, yield 0.1 g.

EXAMPLE 20

The compound prepared in Example 19 is tested for enzyme inhibition activity. Significant activity ($IC_{50}$) is found.

EXAMPLE 21

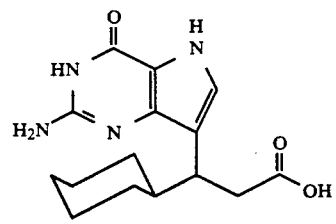

3-(2-Amino-4-oxo-3H,5H-pyrrolo[3,2-d]pyrimidin-7-yl)-3-cyclohexylpropanoic acid is prepared in this example. A solution of the compound obtained in Example 15 (83 mg, 0.28 mmol) in trifluoroacetic acid (TFA) (15 ml) is hydrogenated with $PtO_2$ (83 mg) at 60 lb/in² for 24 h. The catalyst is filtered off through a Celite bed, and the filtrate is evaporated at 25° C. The residue is suspended in $H_2O$ (8 ml), and adjusted to pH 8.5 by conc. $NH_4OH$ and filtered through a Whatman filter paper to remove brown colored impurities. The colorless filtrate is adjusted to pH ~6.8, and the precipitated compound is filtered, washed with $H_2O$, and dried, yield 65 mg (77%), mp >300° C.

EXAMPLE 22

The compound prepared in Example 21 is tested for enzyme inhibition activity as in Example 9. At 1 mM phosphate the $IC_{50}$ is 0.097 μM and at 50 mM phosphate the $IC_{50}$ is 1.0 μM.

EXAMPLE 23

A compound of the present invention is prepared wherein X is $PO(OH)_2$. The nitrile group of the compound of Example 13 is converted to the corresponding amide by treatment with sulfuric acid. Using a Hoffman degradation reaction, the amide is converted to the corresponding amine, which is then converted to the corresponding pyridinium salt using a pyrillium salt. Conversion of the salt to the corresponding halide is accomplished using sodium bromide, which is then converted to the phosphonic ester using triethyl phosphite. Hydrolysis of the ester using trimethylsilylbromide yields the corresponding phosphonic acid wherein "n" is 1 and "m" is 0.

EXAMPLE 24

This Example makes a compound of the present invention by stepping up the number of carbon atoms from "m" is 0 to "m" is 1. The nitrile group of the compound of Example 13 is reduced to the corresponding aldehyde, which is then converted to the corresponding alcohol. Using phosphorous tribromide the alcohol is converted to the corresponding alkyl bromide, which is then converted to the nitrile compound of the present invention wherein m is 1 using potassium cyanide.

EXAMPLE 25

In this example a compound of the present invention is prepared wherein "p" is 1 and "Y" is oxygen. The alcohol prepared as an intermediate in the previous example is converted to the corresponding diethyl phosphonomethyl ether using diethylchloromethyl phosphonate. Removal of the ethyl groups of the ester is accomplished using trimethylsilylbromide to give the phosphonic acid.

EXAMPLE 26

In this example a compound of the present invention is made wherein "Y" is NH and "X" is $SO_2NH_2$. The nitrile group of the compound of Example 13 is reduced to the amine using standard catalytic hydrogenation with palladium in acidic media (usually 0.01N to 1N HCl), which is then converted to the sulfamide using sulphamoyl chloride.

EXAMPLE 27

In this example a compound of the present invention is prepared wherein "X" is COOH and "Y" is NH by reacting the methyl amine intermediate prepared in the previous example with chloroacetic acid.

EXAMPLE 28

In this example a compound of the present invention is prepared wherein "X" is $PO(OH)_2$ and "Y" is NH by reacting the methyl amine intermediate prepared in Example 27 with diethylchloromethyl phosphonate, and reacting the resulting product with trimethylsilylbromide.

EXAMPLE 29

In this example a compound of the present invention is prepared wherein "X" is $So_2NH_2$ and "Y" is oxygen by reacting the alcohol intermediate prepared in Example 24 with sulphamoyl chloride.

EXAMPLE 30

In this example a compound of the present invention is prepared wherein $R^1$ is H, $R^2$ is phenyl, $R^3$ and $R^4$ are hydrogen, m is 0, n is 1, p is 0, and X is CN. A modification of the procedure disclosed in Mu-Ill Lim, et al., *J. Org. Chem.*, Vol. 44, No. 22, 3826 (1979) is used. A mixture of the compound of Example 5 and dimethylformamide dimethyl acetal is reacted at room temperature for two days and then evaporated to dryness in vacuo. The residue is crystallized to give the pure N-(dimethylamino)methylene derivative, which is cyclized with saturated methanolic ammonia to give the desired end product.

EXAMPLE 31

In this example a compound of the present invention is prepared wherein $R^1$ is $OCH_3$, $R^2$ is phenyl, $R^3$ and $R^4$ are hydrogen, m is 0, n is 1, p is 0, and X is CN. Using the compound B of Example 8, the S-methyl group is oxidized to methylsulfone, which then is converted to the final methoxy compound by treatment with sodium methoxide in methanol.

EXAMPLE 32

In this example a compound of the present invention is prepared wherein X is tetrazole. The compound of Example 13 is treated with lithium azide in the presence of ammonium chloride as a catalyst in dimethylformamide (DMF) at 100 degrees C. to give the desired tetrazole.

EXAMPLE 33

In this example a compound of the present invention is prepared wherein X is triazole. The compound of Example 19 is treated with hydrazine hydrate to give the corresponding hydrazide, which is then treated with imino ether to give the desired triazole.

EXAMPLE 34

The compound prepared in Example 10 is tested for enzyme inhibition activity as in Example 9. At 1 mM phosphate the $IC_{50}$ is 0.012 µM and at 50 mM phosphate the $IC_{50}$ is 2.0 µM.

EXAMPLE 35

In this example an amidine compound of the present invention is prepared, i.e., wherein X in the recited generic formula is $CNHNH_2$. The compound A from Example 8 is reacted with sodium methoxide in methanol at room temperature for about 2 days to give a methylimidate intermediate. The intermediate is then reacted with ammonia in methanol to give the amide product.

What is claimed is:

1. A PNP inhibitor comprising a compound of the formula

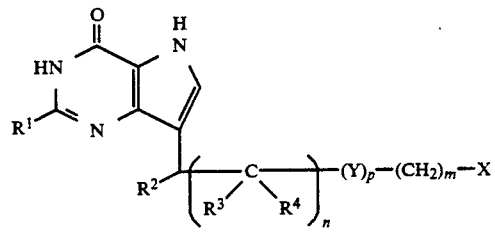

wherein $R^1$ is H, $NH_2$, or $OCH_3$, $R^2$ is phenyl optionally substituted with at least one halogen, hydroxy, $C_{1-4}$ alkyl, $C_{1-4}$ alkoxy, or trifluoromethyl, $R^3$ and $R^4$ are independently H or $C_{1-4}$ alkyl, m is 0-4, n is 0-6, p is 0-1, X is CN, $CSNH_2$, $PO(OH)_2$, COOH, $SO_2NH_2$, $NH_2$, OH, $CNHNH_2$, tetrazole, or triazole, $COR^5$ where $R^5$ is $C_{1-4}$ alkyl, $CF_3$, $NH_2$, or $OC_{1-4}$ alkyl, and Y is O or NH.

2. The inhibitor of claim 1 wherein $R^2$ is unsubstituted.

3. A compound according to claim 1, wherein $R^1$ is $NH_2$, $R^2$ is unsubstituted, m is 1 and n is 0.

4. The inhibitor of claim 3 wherein $R^2$ is phenyl.

5. The inhibitor of claim 4 wherein X is CN.

6. The inhibitor of claim 4 wherein X is COOH.

7. The inhibitor of claim 4 wherein X is $CONH_2$.

8. A compound according to claim 1, wherein m is 1, n is 1 and p is 0.

9. A compound according to claim 1, wherein m is 1, n is 0 and p is 0.

10. The compound of claim 1 wherein n is 1-4, m is 0, $R^3$ and $R^4$ are each H, an X is OH, CN, COOH, or $COR^5$ wherein $R^5$ is $NH_2$ or $OC_{1-4}$ alkyl.

11. The compound of according to claim 10 wherein $R^1$ is H.

12. A compound according to claim 11 wherein $R^1$ is $NH_2$.

13. A compound according to claim 11 wherein n is 1 or 2.

14. A compound according to claim 11 wherein $R^2$ is phenyl, dichlorophenyl, chlorophenyl, or trichlorophenyl, n is 1 or 2, and X is COOH, CN, OH, or $COR^5$ wherein $R^5$ is $NH_2$ or $OC_{1-4}$ alkyl.

15. A compound according to claim 15 wherein X is OH or CN.

16. A compound according to claim 11 wherein $R^2$ is phenyl, dichlorophenyl, chlorophenyl, or trichlorophenyl, n is 1, and X is COOH, CN, OH, or $COR^5$ wherein $R^5$ is $NH_2$ or $OC_{1-4}$ alkyl.

17. A compound according to claim 17 wherein X is CN or $CONH_2$.

18. The inhibitor of claim 1, further comprising a pharmaceutically acceptable carrier or diluent.

19. A method for the selective suppression of mammalian T-cell function without diminished effect on humoral immunity comprising administering to a subject an effective amount of the PNP inhibitor of claim 1.

20. A method for the selective suppression of mammalian T-cell function without diminished effect on humoral immunity comprising administering to a subject an effective amount of the PNP inhibitor of claim 5.

21. A method for the selective suppression of mammalian T-cell function without diminished effect on humoral immunity comprising administering to a subject an effective amount of the PNP inhibitor of claim 6.

22. A method for the selective suppression of mammalian T-cell function without diminished effect on humoral immunity comprising administering to a subject an effective amount of the PNP inhibitor of claim 7.

23. A pharmaceutical composition for the selective suppression of mammalian T-cell function without diminished effect on humoral immunity comprising an effective amount of the PNP inhibitor of claim 1 and a pharmaceutically acceptable carrier or diluent.

24. A pharmaceutical composition for the selective suppression of mammalian T-cell function without diminished effect on humoral immunity comprising an effective amount of the PNP inhibitor of claim 5 and a pharmaceutically acceptable carrier or diluent.

25. A pharmaceutical composition for the selective suppression of mammalian T-cell function without diminished effect on humoral immunity comprising an effective amount of the PNP inhibitor of claim 6 and a pharmaceutically acceptable carrier or diluent.

26. A pharmaceutical composition for the selective suppression of mammalian T-cell function without diminished effect on humoral immunity comprising an effective amount of the PNP inhibitor of claim 7 and a pharmaceutically acceptable carrier or diluent.

* * * * *

UNITED STATES PATENT AND TRADEMARK OFFICE
CERTIFICATE OF CORRECTION

PATENT NO. : 5,189,039
DATED : February 23, 1993
INVENTOR(S) : Shri NIWAS et al.

It is certified that error appears in the above-indentified patent and that said Letters Patent is hereby corrected as shown below:

```
Col. 14, line 55, change "an" to --and--;
         line 57, delete "of";
         line 59, change "11" to --10--;
         line 61, change "11" to --10--;
         line 63, change "11" to --10--;
         line 67, change "15" to --14--.
Col. 15, line 1, change "11" to --10--; and
         line 5, change "17" to --16--.
```

Signed and Sealed this

Twenty-ninth Day of March, 1994

Attest:

BRUCE LEHMAN

*Attesting Officer*          *Commissioner of Patents and Trademarks*